(12) United States Patent
Normant et al.

(10) Patent No.: US 6,696,267 B2
(45) Date of Patent: Feb. 24, 2004

(54) METHODS AND COMPOSITIONS FOR SCREENING ICRAC MODULATORS

(75) Inventors: Emmanuel Normant, Antony (FR); Janet Allen, Meudon (FR); François Roman, Vitry sur Seine (FR); Gilles Brunelle, Antony (FR)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/821,811

(22) Filed: Mar. 30, 2001

(65) Prior Publication Data

US 2002/0034728 A1 Mar. 21, 2002

(30) Foreign Application Priority Data

Apr. 3, 2000 (EP) .............................. 00400923

(51) Int. Cl.[7] .............................. C12Q 1/02; C12Q 1/68; C12Q 1/48; C12N 15/63; C12N 5/10
(52) U.S. Cl. .............................. 435/29; 435/6; 435/455; 435/354; 435/372.3; 435/372; 435/18
(58) Field of Search ............................. 435/6, 455, 354, 435/372.3, 372, 18, 29

(56) References Cited

U.S. PATENT DOCUMENTS 6,004,808 A    12/1999   Negulescu et al. .........   435/325

FOREIGN PATENT DOCUMENTS

| EP | 0 982 398 | | 3/2000 |
|---|---|---|---|
| WO | WO 93/13423 | * | 7/1993 |
| WO | WO98/08979 | | 3/1998 |
| WO | WO00/40614 | | 7/2000 |

OTHER PUBLICATIONS

Zlokarnik et al., Quantitation of transcription and clonal selection of single living cells with B–Lactamase as reporter, 1998, Science, vol. 279, pp. 84–88.*

Kerschbaum et al., Ion channels, Ca2+ signaling, and reporter gene expression in antigen–specific mouse T cells, 1997, The Journal of Immunology, vol. 159, pp. 1628–1638.*

Karttunen et al., Measurement of ligand–induced activation in single viable T cells using the lacZ reporter gene, 1991, Proc. Natl. Acad. Sci. USA, vol. 88, pp. 3972–3976.*

Bridgland–Taylor MH et al.: "Validation of a high throughput screen to detect potential modulators of Ca2+ release – activated Ca2+ channels in Jurkat T–cells" British Journal of Pharmacology, vol. 125, No. Proc. Suppl, Dec. 1998, p. 82.

Loh C et al.: "T–cell receptor stimulation elicits an early phase of activation and a later phase of deactivation of the transcription factor NFAT1" Molecular and Cellular Biology, vol. 16. No. 7, Jul. 1996, pp. 3945–54.

Fanger C et al.: "characterization of T cell mutants with defects in capacitative calcium entry: Genetic evidence for the physiological roles of CRAC channels" Journal of Cell Biology, vol. 131, No. 3, Nov. 1995, pp. 655–667.

* cited by examiner

*Primary Examiner*—James Ketter
*Assistant Examiner*—Daniel M. Sullivan
(74) *Attorney, Agent, or Firm*—Nixon & Vanderhye, P.C.

(57) ABSTRACT

The present invention relates to compositions and methods directed at screening or characterizing compounds that modulate the activity of calcium channels in cells preferably, calcium-release activated channels in cells. The compositions and methods can be used to produce inhibitors or activators of said channel, which represent leads or candidate therapeutic drugs for treating various pathological conditions. More specifically, the method comprises (a) contacting a test compound and a calcium channel activator, preferably an Icrac activator with a population of calcium channel expressing cells, preferably Icrac expressing cells containing a reporter construct comprising a reporter gene under the control of a NFAT-inducible promoter, and (b) determining the activity of the test compound on the calcium release-activated channel by assessing the reporter gene expression in said cells.

17 Claims, 8 Drawing Sheets

METHODS AND COMPOSITIONS FOR SCREENING ICRAC MODULATORS

FIELD OF THE INVENTION

Figure 1:
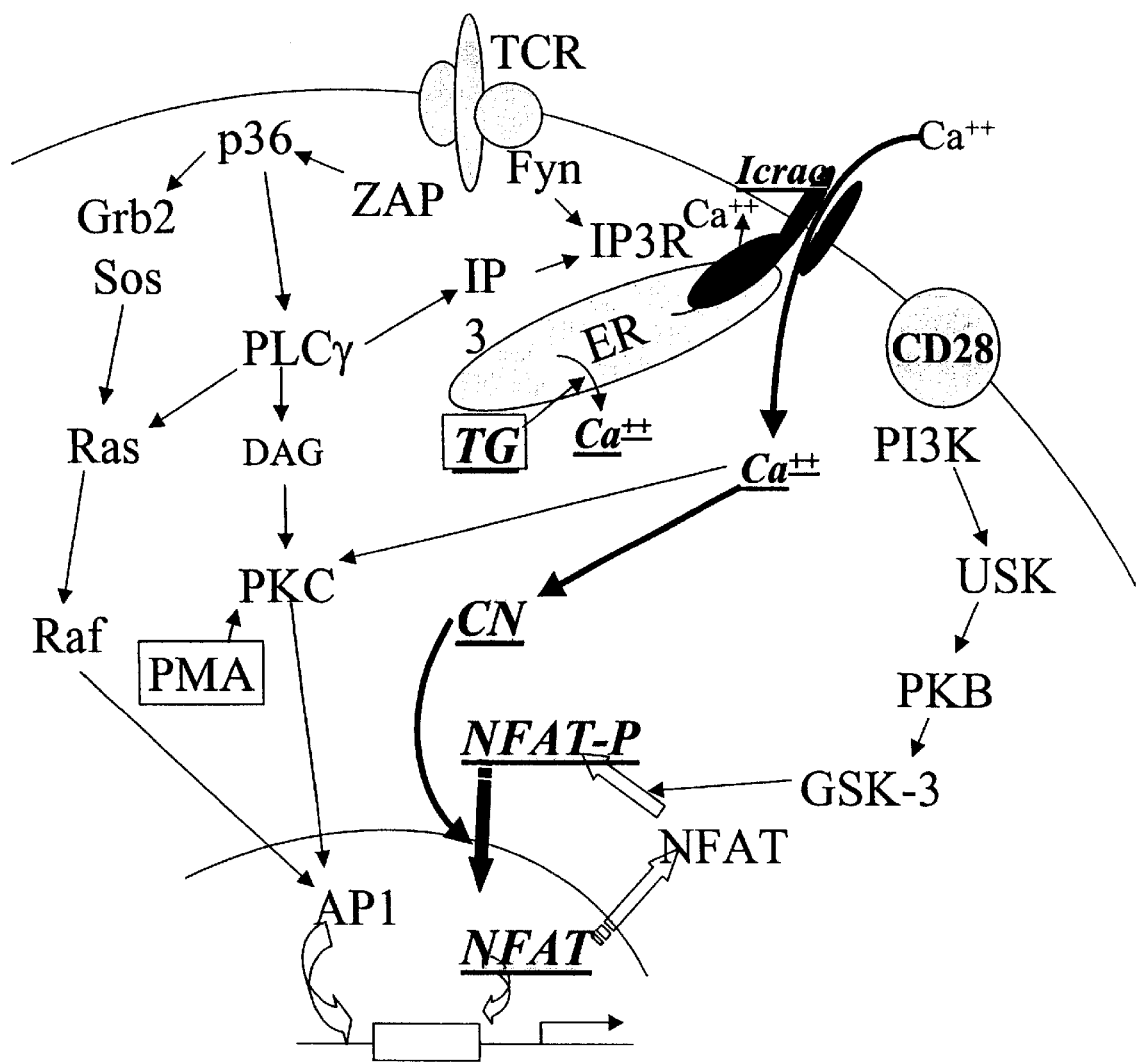

The present invention relates generally to compositions and methods for screening compounds that modulate calcium entry or calcium-mediated activity within cells. More specifically, this invention discloses compositions and methods, including cell based assays, directed at screening or characterizing compounds that modulate the activity of calcium-release activated channels in cells. The compositions and methods can be used to produce inhibitors or activators of said channel, which represent leads or candidate therapeutic drugs for treating various pathological conditions.

BACKGROUND OF THE INVENTION

Calcium influx and regulation play a critical role in many cellular processes in both excitable and non-excitable mammalian cells, including exocytosis, gene expression, cell differentiation, cell activation, contraction, etc. In non-excitable cells, such as immune cells, calcium concentration and flux are regulated essentially by voltage-independent $Ca^{++}$ channels (sometimes referred to as capacitative calcium entry (CCE)), designated store-operated channels (SOC) or receptor-operated channels (ROC). The activity of these channels is essential in the regulation of calcium entry and participates directly in many important cellular processes such as cell activation or maturation for instance. A particularly important type of store-operated calcium channel is the Calcium release-activated channel (Icrac), which is opened in response to depletion of intracellular calcium stores and mediates various intracellular transduction signals.

For instance, the Icrac channel is involved in T cell activation following binding of an antigen to the T Cell Receptor (TCR). The fill activation of T lymphocytes is due to the stimulation of the TCR/CD3 complex and CD2, CD4 or CD28 (see for review (1)). Upon antigenic stimulation of T-cells, (2) nuclear factor of activated T cells (NFAT) is required for the production of immunoregulatory molecules such as interleukins, IFN-γ, or TNF-α (3). NFAT is a complex including a constitutive cytoplasmic component expressed in resting immunomodulatory cells such as T and B-cells, which translocate to the nucleus, and an inducible nuclear component consisting of dimers of fos- and jun-family proteins. Dephosphorylation of the cytoplasmic component of NFAT by $Ca^{++}$/calmodulin-dependent serine/threonine phosphatase, calcineurin, induces its translocation to the nucleus (4). Prolonged elevation of $[Ca^{++}]_i$ level, beyond the initial transient increase resulting from the emptying of calcium intracellular pools, is required to maintain calcineurin phosphatase in activated state. After stimulation of immunomodulatory cells such as T-cell by external components, this calcium mobilization is the outcome of capacitative calcium entry, a process originated by the depletion of $Ca^{++}$ store and the inflow of extracellular calcium through the specific Calcium release-activated $Ca^{++}$ channel (Icrac) (5, 6). Capacitative $Ca^{++}$ entry is triggered by stimulation of various receptors such as T-CR, B-CR, high affinity IgE receptor (FcεRI) and IgG receptor (FcγRI) (via PLCγ, and IP3 receptor activation), CD40 (3) or by calcium ionophore (6, 7). Inhibitors of endoplasmic reticulum $Ca^{++}$/ATPase pump (thapsigargin (TG)) (Thastrup et al., PNAS 87 (1990) 2466, ref (9)) or cyclopiazonic acid (CPA) (8)) directly deplete intracellular calcium stores and lead to Icrac activation.

It has also been shown that Icrac is expressed by other blood cells such as T cells. Because of its role in interleukin production, Icrac is seen as a very interesting target for novel anti-inflammatory and immunosuppressing drugs or lead compounds. Furthermore, it has recently become clear that an Icrac like current is also present in endothelial cells (Am. J. Physiol. 269 (1995) C733, ref (10)) and in epithelial cells (J. Biol.Chem. 270 (1995) 169, ref (12)). Since radical damage could be linked to $Ca^{++}$ inflow in these cells, it is thought that Icrac blockers would have a positive effect. In addition, since $Ca^{++}$ inflow blockade leads to the IL2 synthesis blockade, Icrac blockers are potentially useful in proliferative or progressive diseases such as malignant tumors.

Icrac thus represents a very powerful target for screening of compounds with high therapeutic potential. However, the use of this target has been hampered so far by the fact that this channel has not been isolated or cloned in the art.

SUMMARY OF THE INVENTION

The present invention provides compositions and methods that allow an efficient screening for Icrac modulators. The invention discloses cell based assays allowing selective and efficient determination of the effect of any test compound on Icrac activity. The methods of this invention can be used to screen large amounts of test compounds, including libraries of compounds, on a high throughput basis, by reducing the number of false positives, providing increased selectivity and easy monitoring of the effect of any compound. Icrac modulators represent high potential leads or candidate drugs for the treatment or alleviation of various pathological conditions, including immune-related diseases such as auto-immune diseases, inflammation, allergy, asthma, cancers or other cell proliferative disorders.

In accordance with the present invention, a method is provided for screening a compound that modulates calcium channel activity, preferably calcium release-activated channel (Icrac) activity, comprising:
  a. contacting a test compound and a selective calcium channel activator, preferably an Icrac activator with a population of calcium channel expressing cells, preferably Icrac expressing cells, said cells further containing a reporter construct comprising a reporter gene under the control of a NFAT-inducible promoter, and
  b. determining the activity of the test compound on the calcium release-activated channel by assessing the expression of the reporter gene in said cells.

In a particular embodiment, the determination of the reporter gene expression comprises:
  (i) contacting the cells of a) with a substrate of the reporter gene expression product, and
  (ii) determining the activity of the test compound on the calcium release-activated channel by assessing the hydrolysis of the substrate in said cells.

The reporter gene expression (e.g., hydrolysis of the substrate) can be correlated directly to the activity of the test compound: elevated expression levels (e.g. elevated levels of hydrolysis product) or an increase in expression levels (of the hydrolysis product) as compared to a control situation in the absence of the test compound indicates that the compound stimulates Icrac; low expression levels (e.g., low levels of hydrolysis product) or a decrease in the expression levels (of the hydrolysis product) as compared to a control situation in the absence of the test compound indicates that the compound inhibits Icrac.

Within a preferred embodiment, the cells are contacted with a selective Icrac activator, that preferentially does not activate Protein Kinase C ("PKC"). More preferably the selective Icrac activator does not contain phorbol ester myristate acetate (PMA).

According to a preferred embodiment, the reporter gene is a β-lactamase gene and the substrate is a substrate of β-lactamase.

According to other preferred embodiments, the substrate is a ratiometric substrate, and/or the population of Icrac-expressing cells comprises a culture of blood cells, particularly lymphocytes or mastocytes.

In a particular variant of the present invention, the method further comprises the screening of the active test compounds detected in step b) above to determine which of these compounds modulate the expression activity of the reporter gene product (e.g., β-lactamase) in a non-NFAT dependent manner. This secondary screen allows to increase the selectivity of the method, by eliminating various test compounds which would modulate β-lactamase activity or, more generally, cell metabolism without specifically modulating Icrac (e.g., cytotoxic compounds, compounds that alter DNA or protein synthesis in the cells, etc.).

In order to discard as many as possible Icrac-unrelated hits, another secondary assay may be performed, in addition to of the above-mentioned secondary assay. This assay uses a stable cell line where a NFAT-driven gene reporter expression is triggered by activation of a Gq-coupled receptor such as the muscarinic receptor 1 (M1). In this case, the only difference in the activation pathway is the trigger itself (Icrac or M1) but the whole downstream process stays identical.

The present invention can be used to screen various test compounds, including libraries of compounds (e.g., combinatorial libraries), either sequentially or in parallel, and to identify Icrac blockers or stimulators. The invention is also applicable to assay the activity of Icrac modulators.

Other aspects of the present invention reside in kits for use in performing the above methods, cell cultures, supports and other reagents, as well as the use of said Icrac modulators for pharmaceutical purposes.

DETAILED DESCRIPTION OF THE INVENTION

As indicated above, the present invention provides compositions and methods to analyse the activity of the Icrac channel and to screen for compounds that modulate said activity. The present invention describes compositions and methods allowing specific detection of Icrac activation via a reporter gene system. The present invention is suitable for high throughput screening of large amounts of compounds, and allows the identification of compounds with higher selectivity for calcium channels than was possible with previous strategies. As will be discussed below, the present methods and compositions provide significant advantages and broad spectrum of applications.

Calcium channels aid in the transportation of calcium through the plasma membrane and regulate the flux of calcium between the cell and its environment. Calcium channels can be characterised by their kinetic profile and their cell type physiology and pathology.

The invention is more specifically based on the use of a reporter system to measure the activity of Icrac. More particularly, the invention uses a reporter system that monitors the Icrac-induced, NFAT-dependent production of a reporter gene product within cells. As indicated above, NFAT ("Nuclear factor of activated T cells") is produced and activated within T cells in response to Icrac stimulation.

NFAT is a molecular complex including a constitutive cytoplasmic component expressed in resting T-cells and an inducible nuclear component consisting of dimers of fos- and jun-family proteins. Upon Icrac stimulation and Icrac-mediated calcium influx, the $NFAT_c$ translocates to the nucleus, where it specifically binds particular DNA regions (NFAT responsive or inducible promoter regions) and mediates gene expression. NFAT thus represents an interesting marker of Icrac activity within the cells, in particular within the cells of the immune system.

However, NFAT production/translocation may also result from or be influenced by other signalling pathways in the cells, including the Protein Kinase C (PKC) pathway for instance. In particular, many secondary pathway components are well known to interact with the activation of the NFAT promoter and, as a consequence, with the readout of the assay (see FIG. 1). Among them, one can cite the AP-1 activators (e.g. PLCγ/PKC pathways) or the calcineurin independent NFAT dephosphorylation pathway (CD28/PI3 Kinase pathway).

The invention now proposes to screen Icrac activity by monitoring the Icrac-induced NFAT specific production of reporter molecules within the cell. The invention more specifically provides a novel cellular reporter assay that allows to specifically monitor the Icrac activity in a reliable manner.

A first object of this invention resides more specifically in a method for screening a compound that modulates calcium channel activity, preferably calcium release-activated channel (Icrac) activity, comprising:

a. contacting a test compound and a selective calcium channel activator, preferably an Icrac activator with a population of calcium channel expressing cells, preferably Icrac expressing cells, said cells further containing a reporter construct comprising a reporter gene under the control of a NFAT-inducible promoter, and b. determining the activity of the test compound on the calcium channel, preferably a calcium release-activated channel by measuring the reporter gene expression.

In a preferred embodiment, the Icrac activator (direct or indirect) in step a) is a selective Icrac activator, e.g. any product, treatment or condition allowing selective depletion of internal calcium stores. More preferably, the selective activator does not contain any co-stimulator of alternative signalling pathways such as PKC, to ensure higher selectivity of the method.

In another preferred embodiment, the method further comprises the screening of compounds that modulate reporter gene expression in a non-NFAT dependent manner or through a different activation pathway.

Each step and/or element of the method will now be described in more details.

The Cell Population

The invention comprises contacting various compounds and reagents with a population of calcium channel expressing cells, preferably Icrac-expressing cells that contain a particular reporter construct.

The cell population to be used in the invention preferably comprises mammalian Icrac-expressing cells, such as blood cells, epithelial cells or endothelial cells. Preferred cell populations comprise blood cells, such as lymphocytes (in particular T and B lymphocytes), mastocytes or dendritic cells, for instance. The cells are preferably established as cell lines, that can be cultured and stored. The cells can be of various mammalian origin, including human, rodent, bovine, porcine, canine, etc. Preferred cells are of human or rodent (e.g., murine, rat) origin. Typical examples of such cells include the Jurkat T cell line and the P815 mastocyte cell line. It should be understood that any other Icrac-expressing cell may be used in this invention.

In this regard, an object of this invention resides in a culture of lymphocytes (or lymphocyte-derived cells) as well as mastocytes (or mastocyte-derived cells) that contain a reporter construct as described below. More specifically, the invention concerns any mastocyte-derived cell line, such as the P815 cell line, comprising a reporter construct as described below.

The invention also relates to any population of rodent immune cells, in particular any population of murine or rat immune cells, that comprises a reporter construct as described below. The invention describes the production of such cells, and demonstrates that they can be used to screen Icrac-mediated NFAT-dependent β-lactamase production with efficacy, sensitivity and reproducibility.

For performing the instant invention, it is not necessary that pure cell populations be used. In particular, the cell population may comprise 20% of non Icrac-expressing cells or of cells that do not contain the reporter construct. However, it is preferred to use cell populations that preferably comprise at least 80% of cells expressing the Icrac channel and containing the reporter system in order to increase the efficacy and sensitivity of the method. More preferably, the cell populations comprise at least 85% of these cells and most preferred at least 90%.

The reporter construct contained in the cells comprises a reporter gene under the control of a NFAT-inducible promoter. The construct can be incorporated in a plasmid, vector, virus, episome, YAC, etc., i.e., in any appropriate genetic system that allows maintenance of the construct within the cells. Typical reporter constructs of this invention comprise a plasmid, such as pcDNAIII, pUC, etc. in which at least one copy of the reporter gene and promoter has been inserted. The plasmid may further comprise a marker gene, allowing selection of the recombinant cells that contain the reporter construct. Alternatively, the reporter construct may be integrated into the genome of the cells, by any conventional technique, including recombination, transposons, viral integration etc. In preferred embodiments, the reporter construct is stably introduced into the cells using an extra-chromosomic vector. More preferably, the construct is stable so that it remains present in the cells after several (preferably 100) cell divisions under selection pressure.

The reporter gene can be any nucleic acid encoding a product whose presence in a cell can be determined. The reporter gene may be any cDNA encoding a polypeptide whose presence in a cell can be visualized or determined easily. Examples of such reporter genes include any nucleic acid encoding a polypeptide such as green fluorescent protein (and variants of), β-galactosidase, alkaline phosphatase, luciferase, β-lactamase, or derivatives or homologues thereof.

In a preferred embodiment, the reporter gene is a β-lactamase gene.

The β-lactamase gene may be any nucleic acid molecule encoding a β-lactamase polypeptide, i.e., a polypeptide that can hydrolyse a β-lactam ring. A preferred β-lactamase gene is the bacterial gene as described in Zlokarnik et al (13). It should be understood that any variant, fragment, or analog thereof can be used without deviating from the instant invention.

The NFAT-inducible promoter can be any transcriptional promoter comprising a NFAT-responsive region, i.e., a promoter that is activated in the presence of NFAT and essentially inactive in the absence of NFAT. The promoter can be any promoter functional in mammalian cells, comprising one or several copies of a NFAT binding domain. More preferably, the promoter comprises one or several (e.g. 2–8) copies of the following sequence: GGAGGAAAAACT-GTTTCATACAGAAGGCGT (SEQ ID NO:1) or any derivative or variant thereof. Derivatives include fragments, as well as mutated, modified or deleted sequences, which can be produced by conventional methods known to the skilled artisan. The capacity of said variants/derivatives to confer NFAT-responsiveness to a promoter may be verified by conventional expression technique. A particular and preferred promoter to be used in the reporter construct comprises 3 repeats of SEQ ID NO:1. The sequence of a typical NFAT-inducible promoter is described in Mattila et al (19).

The reporter construct (or any vector containing the same) may be introduced into the cells by conventional techniques, including electroporation, calcium-phosphate precipitation, cationic lipids-, polymer- or liposome-mediated transfection, viral-mediated infection, etc. The cells used in the invention may comprise one or several copies of the reporter construct, preferably between 1 and 10 copies. The cells can be maintained in any culture medium suitable for mammalian cells, including RPMI, DMEM, generally around 37° C. (for human cells), supplemented with conventional additives (antibiotics, amino acids, serum, etc.). Preferred medium comprise elevated Calcium concentration (e.g., above about 1 mM), such as DMEM.

The cells can be cultured and/or stored in any appropriate device (tubes, flasks, bottles, etc.). Cell viability and/or absence of contamination can be verified prior to carrying out the methods of this invention.

The Cellular Assays

Primary Screen

The method of this invention comprises contacting a test compound with the cell population under particular conditions and measuring the reporter gene expression in the cells, as an indication of the effect of the test compound. Typically, the effect of the test compound is compared to the level of expression as measured in the absence of any test compound.

Contacting test compound and activator with Icrac expressing cells

Step a) of the method of this invention more specifically comprises contacting a test compound and an Icrac activator with a population of Icrac expressing cells which contain a reporter construct, as defined above. In a typical embodiment, the method comprises contacting several test compounds, in parallel, in particular at least two test compounds, more preferably at least 10, even more preferably at least 50 compounds. As will be discussed below, the invention is suited for High Throughput Screening of compounds and complete combinatorial libraries can be assayed, i.e., up to thousands of compounds.

The Test Compound

The test compound can be any product in isolated form or in mixture with any other material (e.g., any other product (s)). The compound may be defined in terms of structure and/or composition, or it may be undefined. For instance, the compound may be an isolated and structurally-defined product, an isolated product of unknown structure, a mixture of several known and characterized products or an undefined composition comprising one or several products. Examples of such undefined compositions include for instance tissue samples, biological fluids, cell supernatants, vegetal preparations, etc. The test compound may be any organic or inorganic product, including a polypeptide (or a protein or peptide), a nucleic acid, a lipid, a polysaccharide, a chemical product, or any mixture or derivatives thereof. The compounds may be of natural origin, synthetic origin, including libraries of compounds.

As will be further discussed below, the present invention is particularly adapted for the screening of large numbers of compounds, such as combinatorial libraries of compounds. Indeed, the instant invention provides compositions and methods allowing efficient and simple screening of several compounds in short periods of time. In particular, the instant methods can be partially automated, thereby allowing efficient and simultaneous screening of large sets of compounds.

Generally, the activity of the test compound(s) is unknown, and the method of this invention is used to identify compounds exhibiting the selected property (e.g, Icrac modulators). However, in particular instances where the activity (or type of activity) of the test compound(s) is known or expected, the method can be used to further characterize said activity (in terms of specificity, efficacy, etc.) and/or to optimise said activity, by assaying derivatives of said test compounds.

Preferably, the test compound(s) is (are) contacted with the cells in the presence of an Icrac activator. Indeed, the modulatory effect of the test compound(s) can be assessed preferentially where the Icrac channel is in activated status. To that effect, the cells are contacted with an Icrac activator, either before being contacted with the compound(s), or after or simultaneously. In a typical embodiment, each compound and activator is contacted simultaneously with the cells.

Icrac Activator

As explained above, an advantageous aspect of this invention resides in the targeted monitoring of Icrac activity, more preferably the selective Icrac-mediated activation of NFAT. To that effect, the nature of the Icrac activator (or activation medium or treatment) used in the assay is important, and a preferred and advantageous feature of the methods of this invention resides in the use of selective Icrac activators, which allow a screening for selective Icrac modulators (i.e., blockers or stimulators).

In this regard, the Icrac activator is preferably a calcium-release activator, i.e., a product that promotes depletion of intracellular calcium stores. Indeed, Icrac activation depends on depletion of intracellular calcium stores. In a preferred embodiment, the Icrac activator is a product or treatment or condition that selectively depletes intracellular calcium stores. The Icrac activator may induce directly depletion of intracellular calcium stores (direct effect on Icrac) or through one or several pathways in the cell responsible of Icrac activation (indirect effect on Icrac). In a specific embodiment, the Icrac activator (or activating treatment or medium) does not induce any costimulation of Protein Kinase C (PKC), in particular the activator does not comprise any stimulator of PKC such as phorbol ester myristate acetate (PMA).

Specific examples of Icrac activators for use in the invention include thapsigargin, cyclopiazonic acid, 2,5-di-(tert-butyl)-1,4-hydroquinone (Mason, M. J. et al., J.Biol.Chem. 266, 20856–20862, ref (17)), CD8 antibodies and phytohemmeaglutinin. A preferred Icrac activator to be used in this invention is thapsigargin (Thastrup et al., 1990 supra). Preferably, thapsigargin is used at a concentration ranging between 0.5 and 5 $\mu$M, more preferably below 2 $\mu$M.

In a specific embodiment, the cells are treated in step a) with thapsigargin in the absence of any costimulation of PKC, such as phorbol ester. More preferably, the cells are treated in step a) with thapsigargin alone. According to this embodiment, an Icrac-specific stimulus is used (i.e., thapsigargin) and the PKC pathway is not activated. This particular activation strategy allows to screen more selectively for Icrac activity.

The inventors have discovered that a more optimised signal to noise ratio can be obtained by increasing the calcium concentration in the medium. In particular, when calcium concentrations above 1 mM, preferably between 1 and 3 mM are used, the signal to noise ratio is raised by about 5-fold. Under these conditions, it is possible to screen, on a high throughput basis, with reliable and reproducible results, Icrac blockers in the absence of PKC co-stimulation. More preferred conditions comprise the incubation of the cells in a medium comprising between 1 mM and 2 mM calcium and devoid of phorbol ester.

These conditions represent a preferred embodiment of this invention. In this respect, a particular object of the present invention resides in a method of screening for Icrac blockers (or inhibitors), comprising:

a) contacting a test compound and an Icrac activator with a population of Icrac-expressing cells, said cells further containing a reporter construct comprising a reporter gene under the control of a NFAT-inducible promoter, said cells being cultivated in a medium containing at least 1 mM calcium and lacking phorbol ester, and b) determining the activity of the test compound on the calcium release-activated channel by measuring the reporter gene expression in said cells.

In another specific embodiment of this invention, the cells are contacted with the test compound(s) in the absence of any Icrac activator. This embodiment allows to screen for Icrac activators (or stimulators).

The contacting can be performed in any appropriate support or device, including plate, tube, flask, and the like. Generally, contacting is performed in multi-well plates, allowing multiple assays to be carried out in parallel. Typical supports include microtiter plates, especially the 96-well or 384-well and higher throughput microtiter plate formats, which are easy to manage and easy to illuminate with conventional excitation. Other formats may also be used, including larger microtiter plates or nanotechnologies.

Depending on the support and test compound, varying amounts of cells can be used in the assay. Typically, between $10^3$ and $10^6$ cells are contacted with a compound, more preferably between $10^4$ and $10^5$ cells. As an illustration, in a 96-well microtiter plate, about $10^5$ cells can be incubated in each well and contacted with a compound. In a 384-well microtiter plate, generally less than $10^5$ cells, typically between 1–4 $10^4$ cells are incubated in each well and contacted with a compound (c.f FIG. 7).

The amount (or concentration) of test compound can be adjusted by the user, depending on the type of compound (its toxicity, cell penetration capacity, etc.), the number of cells, the length of incubation period, etc. If necessary, the compound can be contacted in the presence of an agent that facilitates penetration or contact with the cells.

The contacting in step a) can last for about 2 to 6 hours, typically between 3 and 5 hours. Indeed, the cells and various reagents are preferably incubated for a period of time sufficient to allow de novo synthesis of the reporter gene expression product (e.g., β-lactamase). Depending on the type of cells used, this period usually lasts about 3–4 hours. In a typical experiment, the cells and the above reagents are incubated for about 4 hours.

Step b) of the method comprises measuring the reporter gene expression, as an indication of the activity of the test compound.

The measuring can be performed according to various techniques, depending on the type of reporter gene being used. For instance, measuring can comprise dosing optical density or fluorescence emitted, where β-galactosidase or luciferase are used.

In a preferred embodiment, reporter gene expression is measured by assessing the hydrolysis level of a substrate of the reporter gene expression product. This embodiment is suitable for measuring expression of β-lactamase.

Accordingly, in a preferred embodiment, the method comprises:

a. contacting a test compound and a selective Icrac activator with a population of Icrac expressing cells, said cells further containing a reporter construct comprising a reporter gene under the control of a NFAT-inducible promoter, b. contacting the cells of a) with a substrate of the reporter gene expression product, and c. determining the activity of the test compound on the calcium release-activated channel by assessing the hydrolysis of the substrate in said cells.

In a more preferred embodiment, the reporter gene is β-lactamase and step b) of the current method comprises contacting the cells of a) with a substrate of β-lactamase.

In this regard, various substrates can be used to monitor β-lactamase expression, e.g., any product that contains a β-lactam ring and whose hydrolysis can be monitored. Preferred substrates are specific for β-lactamase (i.e., are essentially not hydrolysed in mammalian cells in the absence of β-lactamase), non toxic for mammalian cells, and/or their hydrolysis product can be monitored easily, for instance by fluorescence, radioactivity, enzymatic or any other detection method.

More preferred substrates are ratiometric substrates. Ratiometric substrates are substrates whose hydrolysis can be related directly to the reporter gene product activity regardless of the number of cells. A typical specific, non-toxic and ratiometric substrate for use in the instant invention is CCF2-AM (13). This substrate is conceived as a coumarin linked to a fluorescein molecule by a β-lactam ring. According to the fluorescence resonance energy transfer (FRET) principle, the coumarin (the donor) emits a blue light able to excite the fluorescein (acceptor) which, in turn, produces a green light. Accordingly, the uncleaved substrate emits green light and the product after β-lactamase hydrolysis emits a blue light. The ratio blue upon green fluorescence is directly related to the lactamase activity and not to the number of cells.

The concentration of the substrate can be adjusted by the skilled artisan, depending on the number of cells and Icrac activation conditions used, for instance. Usually, step b) lasts between 15' and 3 hours, preferably less than 2 hours. In a typical embodiment, the cells are contacted with the substrate during about 60 minutes. As a specific illustration, when CCF2-AM was used, an increase in the blue/green ratio could be detected during about two hours. However, a significant (and sufficient) signal could be detected 1 hour after loading the cells with the substrate.

Step c) of the method defined above comprises the determination of the activity of the test compound by assessing the hydrolysis of the substrate in said cells. Typically, the effect of the test compound is compared to the level of hydrolysis of the substrate as measured in the absence of any test compound or to a reference average value determined in the absence of any test compound.

Measuring the hydrolysis comprises essentially a measure (or a determination of the relative quantity) of the hydrolysis product contained in each reaction sample. Said measure can be performed using various techniques known in the art, including fluorescence detection, radioactivity detection, colorimetric detection, enzymatic activity detection, antibody-antigen immune complex detection, etc. In a preferred embodiment, the hydrolysis product is detected and quantified using fluorescence detection. In this regard, various fluorochrome can be used and monitored on cell samples. In a typical experiment, where the CCF2-AM substrate is used, step c) comprises the excitation at about 405 nm and emission at 460 (cleaved substrate) and 535 nm (uncleaved substrate), and the ratio 460/535 is estimated, which is directly correlated to the hydrolysis activity with the cells. It should be understood that any alternative detection method can be employed in the present method.

As indicated above, one of the advantages of these methods is their capacity to screen large numbers of compounds in relatively short periods of time. For instance, in a typical experiment, about 90 compounds are tested in parallel on a 96-well plate and their activity is determined in about 5 hours. The method can be scaled-up to larger plates or device, allowing screening of thousands of compounds every day. Furthermore, the distribution of cells and all reagents in the reaction device can be automated, further increasing the yield and efficacy of the method.

Secondary Screen

In a particular variant of the present invention, the method comprises an additional screening of the compounds that modulate β-lactamase activity in a non-NFAT dependent manner. This secondary screen allows to increase the selectivity of the method, by eliminating various test compounds which would modulate β-lactamase activity or, more generally, cell metabolism, without specifically modulating Icrac activity (e.g., cytotoxic compounds, compounds that alter DNA or protein synthesis in the cells, etc.). Accordingly, in a particular embodiment, the method of this invention further comprises step d) the screening of the compounds obtained in c) in order to eliminate those which modulate β-lactamase activity in a non-NFAT dependent manner. More preferably, step d) comprises contacting the compounds selected in c) with a population of cells comprising a reporter construct comprising a β-lactamase gene under the control of a non-NFAT-inducible promoter, more preferably a CRE-inducible promoter.

This secondary screen can be performed using various populations of cells, in particular mammalian cells, such as HEK cells for instance, or CHO, Jurkat, or Vero cells, for example. The reporter construct can be prepared in the same way as described above, except for the promoter region. In a specific embodiment, the promoter region comprises one or several (1 to 8, preferably 3) CRE sequences (CGTCA), which are responsive to cyclic AMP concentration within cells. Other promoter regions can be used in this secondary assay, such as VIP responsive promoters, or promoters containing NFκB or JNK responsive element, for instance.

Additional or alternative secondary screenings may be performed in order to characterize or profile the selected compounds based on direct mesurement of calcium influx levels such as FLIPR® assays.

Also, additional or alternative secondary screenings may be performed in order to further characterize or profile the selected compounds, including Ca-uptake, electrophysiology of the Icrac channel etc.

In this respect, in order to discard as many as possible Icrac-unrelated hits, another secondary assay may be performed, in addition to or in replacement of the above-mentioned secondary assay. This assay uses a stable cell line where a NFAT-driven gene reporter expression is triggered by activation of a Gq-coupled receptor such as the muscarinic receptor 1 (M1). In this case, the only difference in the activation pathway is the trigger itself (Icrac or M1) but the whole downstream process stays identical.

The invention can be used to screen Icrac modulators, with various therapeutic or research applications.

In this regard, an Icrac modulator can be defined as any compound that modulates the activity of Icrac. It is understood that the term modulate means inhibit, antagonize or block as well as stimulate, increase, facilitate the activity of Icrac. A modulator can be a blocker or a stimulator, as defined below. Modulation of Icrac activity can result from several mechanisms of action. In particular, Icrac modulators can directly interact with Icrac and modulate the Icrac-mediated calcium inflow. As an example, the modulators can interact with Icrac and prevent calcium entry within cells. Another type of modulators according to the present invention is a compound that modulates the activation of Icrac, e.g., a compound that prevents or can modulate upstream activation of Icrac. A further type of modulators according to the present invention comprises compounds that modulate the Icrac-mediated signal transduction. Preferred modulators according to this invention are compounds that modulate Icrac activation and/or that interact with Icrac.

Icrac blockers designate more specifically any compound that blocks (or inhibits, or antagonizes) the activity of an Icrac channel. More preferably, an Icrac blocker is a compound that inhibits at least partially the Icrac activity, typically by at least 20%, as compared to control situation in the absence of said compound. More preferred Icrac blockers inhibit at least 40% of Icrac activity, as measured by NFAT-mediated β-lactamase-dependent hydrolysis of a substrate.

Icrac stimulators designate more specifically any compound that stimulates (or increases, or facilitates) the activity of an Icrac channel. More preferably, an Icrac stimulator is a compound that causes an increase of at least 20% of Icrac activity, as compared to control situation in the absence of said compound. More preferred Icrac stimulators cause an increase of at least 40% of Icrac activity, as measured by NFAT-mediated β-lactamase-dependent hydrolysis of a substrate.

The invention was validated using several molecules known to interact with NFAT activation pathways such as cyclosporin A (CsA) (14, 15), within Icrac expressing cells like T-cells (Jurkat) and mastocytes (16). Since DMSO is a commonly used vehicle for compound solubilization (as well as an anti-inflammatory molecule) its possible interaction with the NFAT-driven activation was also checked. We show here that this reagent, did not hinder the assay at a concentration of about 0.5%. The results presented in this application also illustrate the efficacy of the method since more than 3000 compounds have been screened very rapidly, leading to the identification of 3 efficient modulators of Icrac. Such Icrac modulators represent drug candidate or leads to be used in the treatment of various pathological conditions, including immune diseases (GVHD, autoimmune diseases, inflammation, allergies, asthma, etc.) and proliferative disorders (cancers, stenosis, etc.). The compounds may be used to treat, prevent, correct, alleviate or reduce the pathological condition, either alone or in combination with other pharmaceutically active molecules.

Other aspects and advantages of the present invention will be disclosed in the following experimental section, which should be regarded as illustrative and not limiting the scope of protection.

Abbreviations Used

TG: thapsigargin; CsA: cyclosporin, CPA: cyclopiazonic acid; PHA: phytohemaggutinin; PMA: phorbol myristate acetate; CHX: cycloheximide; Jk-NFAT-blac: jurkat cell line stably expressing b-lactamase under NFAT control; Jk-CMV-blac: jurkat cell line constitutively expressing b-lactamase; p815-NFAT-blac: p815 cell line expressing b-lactamase under NFAT control; HEK-CRE-blac: HEK cell line expressing b-lactamase under CRE control; NFAT: nuclear factor of activated T cells; CRE: cAMP Responsive Element; DMSO dimethyl sulfoxide.

LEGEND TO THE FIGURES

FIG. 1. NFAT-related activation pathway.

Figure 2A:
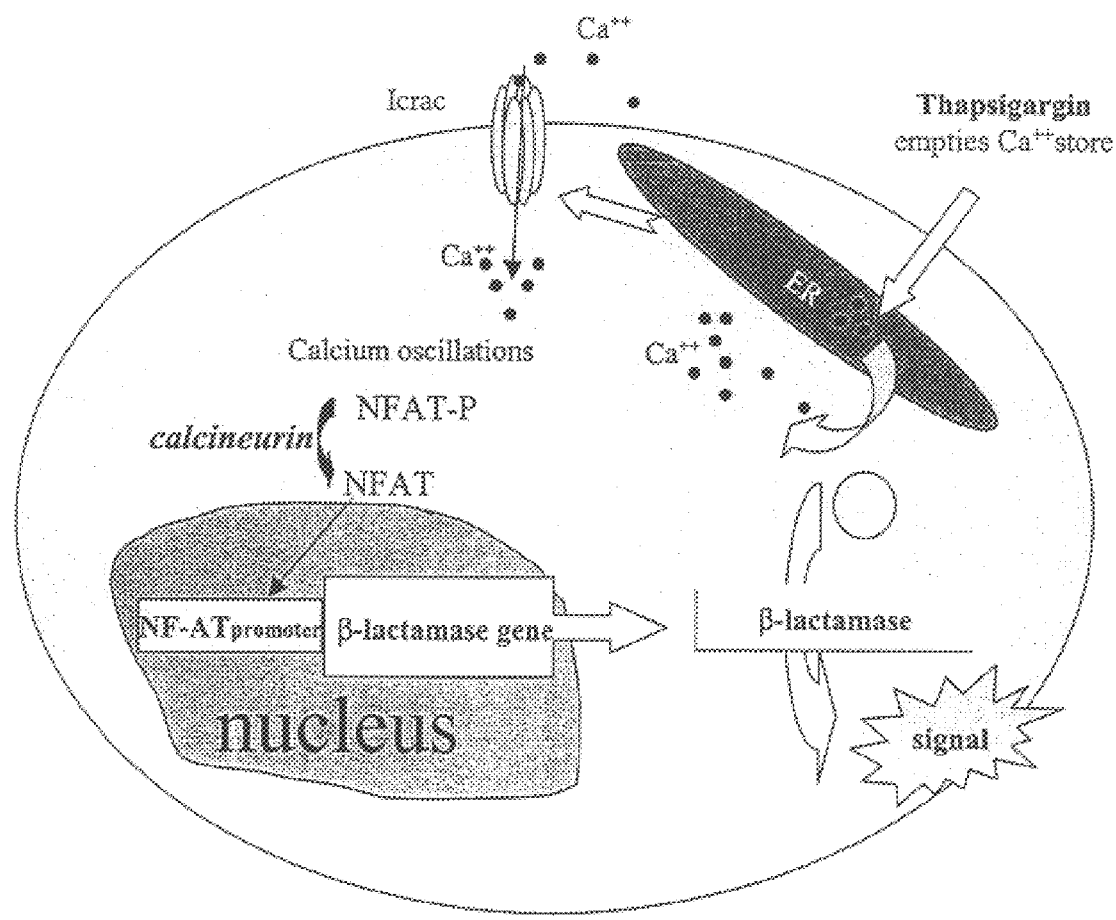

FIG. 2. A) Principle of the gene-reporter cell-based assay. β-lactamase is expressed after activation of NFAT system which is triggered by [$Ca^{++}$] oscillations due to intracellular calcium pool depletion and Icrac stimulation. In this example the hydrolysis of β-lactamase substrate is used to determine the level of expression of β-lactamase.

B) Effect of extracellular [$Ca^{++}$] on the reporter-protein (β-lactamase) synthesis as measured by hydrolysis of CCF2-AM. NFAT-β-lactamase Jurkat cells were stimulated for 4 hrs in RPMI medium (0.4 mM [$Ca^{++}$]) or DME medium (1.8 mM [$Ca^{++}$]) in presence of TG 1 μM.

(C) Effect of Thapsigargin concentration on β-lactamase synthesis. NFAT-β-lactamase Jurkat cells were stimulated for 4hrs with various Thapsigarin concentration in DME medium.

Figure 3:
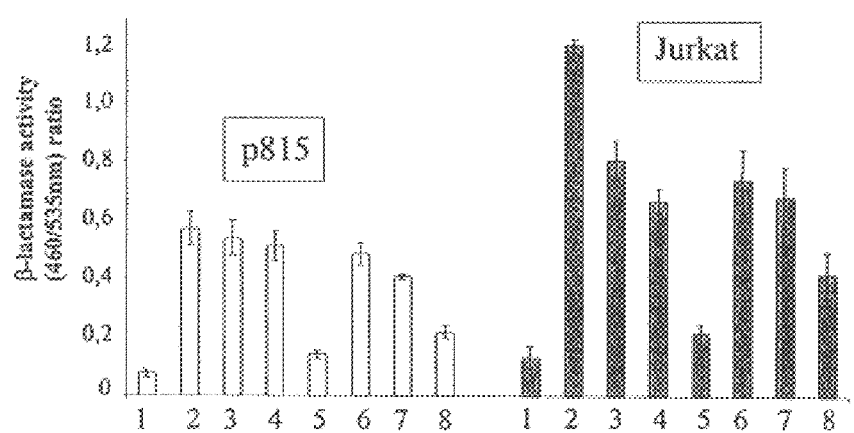

FIG. 3. NFAT-driven gene expression after TG 1 μM stimulation in Jurkat and p815 cells. NFAT-β-lactamase Jurkat cells and NFAT-βlac p815 were incubated with various modulators for 4 h, before substrate loading. 1) control; 2) TG 1 μM+PMA 10 nM; 3) TG 1 μM; 4) CsA 10 nM; 5) CsA 100 nM; 6)DMSO 0.5%; 7) DMSO 1%; 8) DMSO 2%

Figure 4:
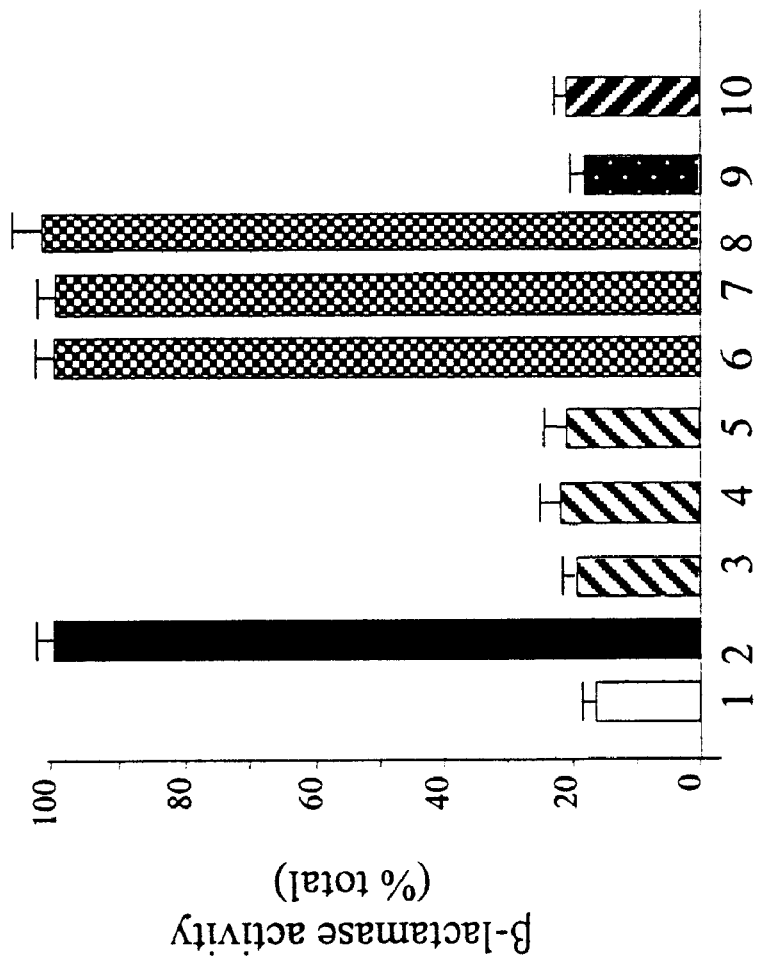

FIG. 4. Effect of various inhibitors on TG-driven β-lactamase synthesis. NFAT-β-lactamase Jurkat cells were incubated with various inhibitors/modulators together with TG 1 μM for 4 h, before substrate loading 1) control, 2) TG 1 μM. TG 1 μM was added with 3) CsA 50 nM, 4) okadaic acid, 5) calyculin, 6) Verapamil 10 μM, 7) Diltiazem 10 μM, 8) Nifedipine 10 μM, 9) cycloheximide 10 μg/ml, 10) DMSO 2%. 100% is defined as cells stimulated with TG 1 μM alone.

Figure 5:
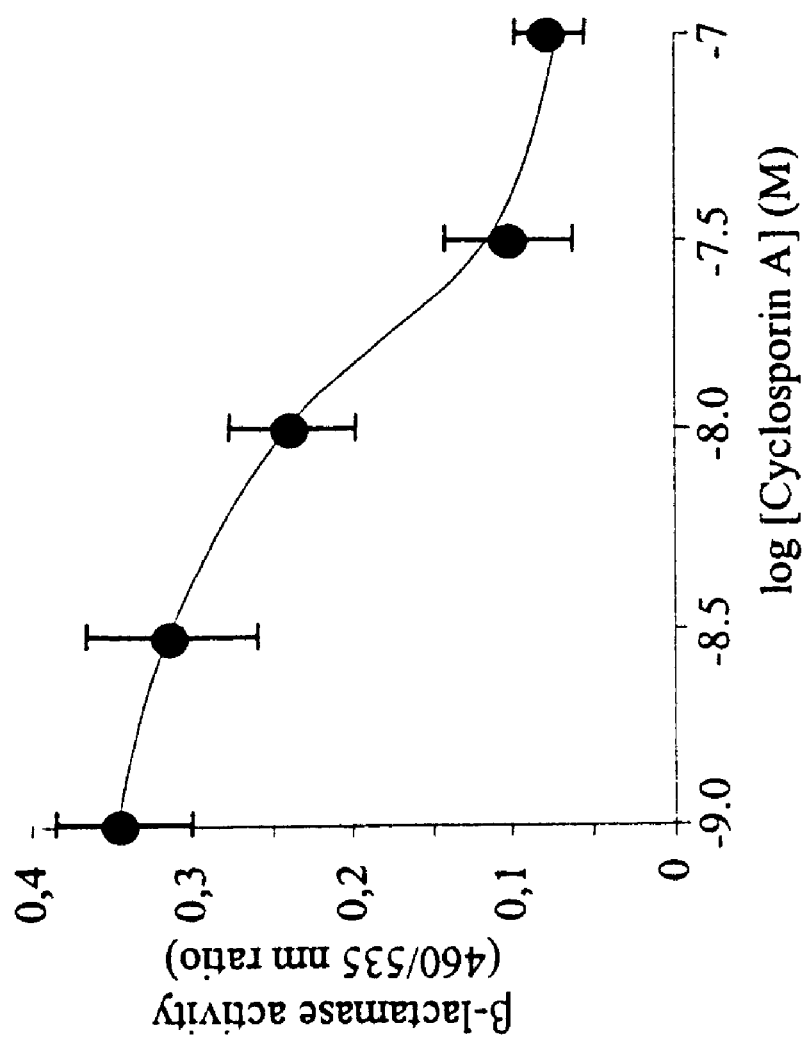

FIG. 5. Effect of Cyclosporin on NFAT-β-lactamase Jurkat cells stimulated by TG. NFAT-β-lactamase Jurkat cells were treated with TG 1 μM in presence of various concentration of Cyclosporin. 100% was defined as stimulated-cells without CsA.

Figure 6:
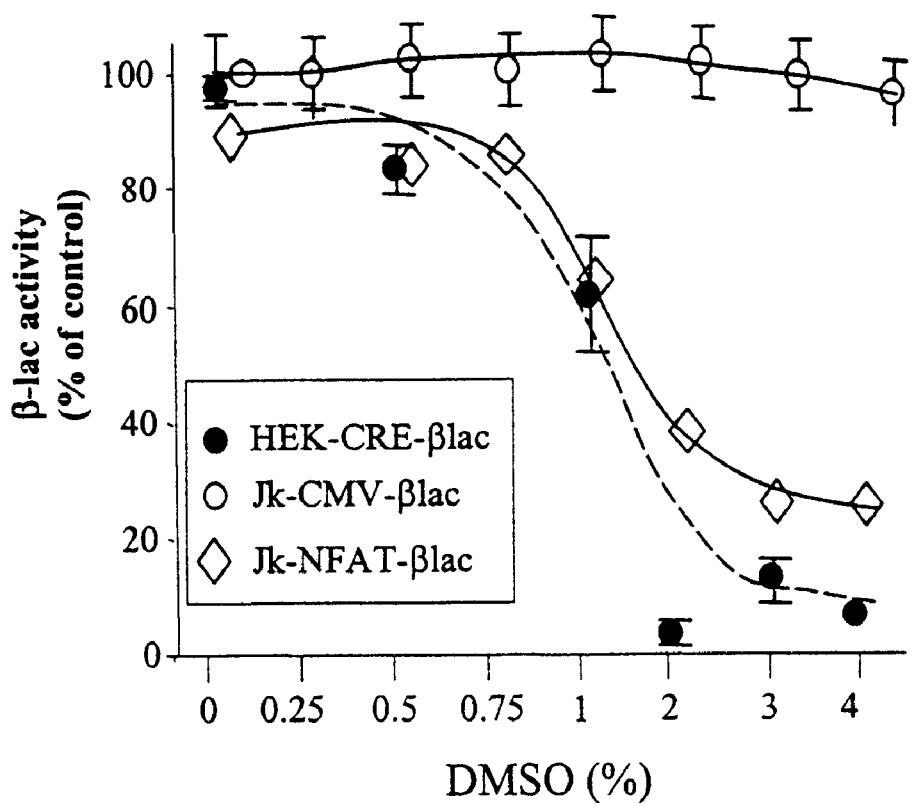

FIG. 6. Effect of DMSO on various cell types and promoters. DMSO 3% were added to wells containing CMV-β-lactamase Jurkat (O) and NFAT-β-lactamase Jurkat (◇) stimulated with TG 1 μM, and CRE-β-lactamase HEK cells stimulated with forskolin 10 μM (●). Results are expressed as the ratio of activities of each cell line without and with DMSO.

Figure 7:
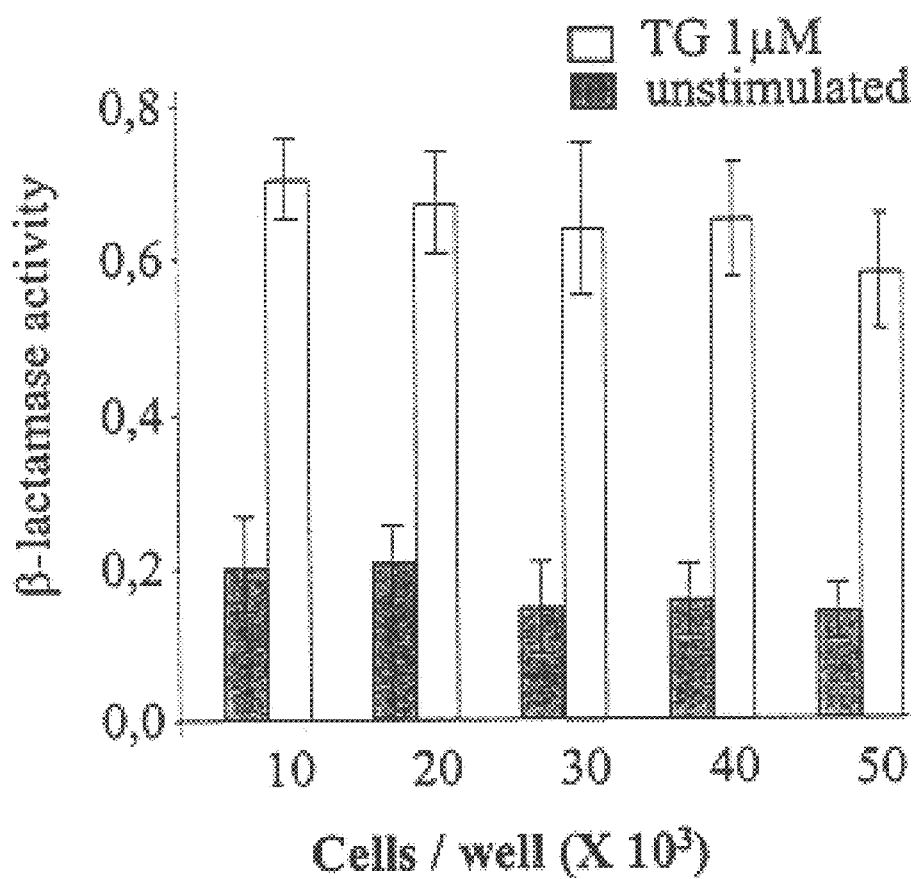

FIG. 7. Stimulation of Jk-NFAT-βlac in a 384 wells plate format.

Table 1 Relative potency of various activators of TG-driven β-lactamase synthesis in NFAT Jurkat cells Table 2 Effect of DMSO on loading capacity of and NFAT-β-lactamase Jurkat cells.

EXAMPLES

1. Materials and Methods

Cell-based Assay

Cell line selection

Jurkat cell lines (Jk-NFAT-βlac) stably transfected with plasmid containing 3×NFAT-β-lactamase reporter gene (for NFAT promoter sequence see (19)), and plasmid containing CMV-β-lactamase (Jk-CMV-βlac), where CMV is a constitutively active promoter as well as HEK cells (HEK-CRE-βlac) with 3×CRE-β-lactamase (the CRE promoter contains CRE box sequence of CGTCA (20)) were obtained from Aurora Biosciences Corp (San Diego, Calif.).

The mastocyte monoclonal cell line (p815-NFAT-βlac) stably transfected with plasmid containing 3×NFAT-β-lactamase were obtained as follow. Cells ($1.10^7$/ml) were electroporated in a 0.4 cm gap cuvette using a BioRad Gene Pulser II at 960 μF and 300V, using 20 μg of pcDNAIII 3×NFAT-β-lactamase Zeomycin expression vector (from Aurora Biosciences Corp; San Diego, Calif.) in DMEM medium. After 48 h, electroporated p815 cells were selected for 2 weeks using 250 μg/ml Zeocin (InVitrogen, Calif.). A pool of TG responding cells were first sorted, using FACS Vantage (Becton Dickinson, Calif.), and a week after, 200 cells were monosorted (one cell per well) from this pool, 15 clones grown up, and were tested as follow.

Gene-reporter assay

Jurkat cells were grown in RPMI 1640 medium supplemented with 10% foetal bovine serum, 2 mM L-glutamine, 1 mM NEAA, 1 mM Na pyruvate, 25 mM HEPES, pH 7.4, gentamicin 100 μg/ml. HEK-293 cells were grown in MEM glutamax, supplemented with 10% FBS, gentamycin 100 μg/ml, HEPES 20 mM. Medium for stable cell propagation contained 250 μg/ml Zeocin (Jk-NFAT-βlac) or 800 μg/ml Geneticin (Jk-CMV-βlac, HEK-CRE-βlac). In a 96-well plate, 1 μM Thapsigargin (TG) was used to stimulate NFAT Jurkat cells ($10^5$ per well), for 4 h at 37° C., 5% CO2, in Dulbecco's Modified Essential Medium ([$Ca^{++}$] 1.8 mM) 10% FBS, gentamycin 100 μg/ml. Cells were then loaded, for 1 h in the dark at room temperature, with 12 μM CCF2-AM (13). Fluorescence was monitored with a Fluostar (BMG, Germany) fluorimeter. Excitation was at 405 nm, and emission record at 460 nm and 535 nm. The ratio (460 nm/535 nm) of fluorescence unit (F.U.) was estimated after correction for background (medium without cells). HEK-CRE-βlac were stimulated using Forskolin 10 μM in the medium mentioned above ($4×10^4$ cells/well). All reagents were added with the stimulator agent (e.g. TG or forskolin), unless noticed.

Optical measurement of Intracellular [$Ca^{++}$].

Loading with 2 μM fura-2-AM was performed with a $3×10^6$ cells suspension for 30 min at 37° C., in Hanks buffer saline solution (HBSS). Cells were washed and resuspended twice to minimize extracellular dye. Fura-2 fluorescence measurements were carried out in a water-jacketed cuvette (room temperature) with continuous stirring, containing 1 ml of the cells suspension. Fluorescence was monitored with a Shimadzu spectrofluorophotometer by continuously (1 sec intervals) collecting excitation signals at 340 nm and 380 nm and emission signal at 510 nm. Maximal and minimal fluorescence were obtained by adding ionomycin 25 μM and EGTA (20 mM) respectively and sequentially at the end of the experiment. The ratio of excitation signals at 340 nm and 380 nm was used to calculate [$Ca^{++}$] as previously described (21) assuming a Kd of 155 nM.

Drugs

Thapsigargin, phorbol ester myristate acetate (PMA), phytohemmagglutinin (PHA), okadaic acid, calyculin, cycloheximide, dry DMSO, cyclopiazonic acid, cyclosporin and Fura-2 were purchased from Sigma. CCF2-AM was from Aurora Biosciences. All cell culture reagents were from LifeTech (Gaithersburgh, Md.). p815 cells were from ATCC (Manassas, Va. ATCC #TIB 64).

2. NFAT Activation in Jurkat Cell Lines

Figure 2B:
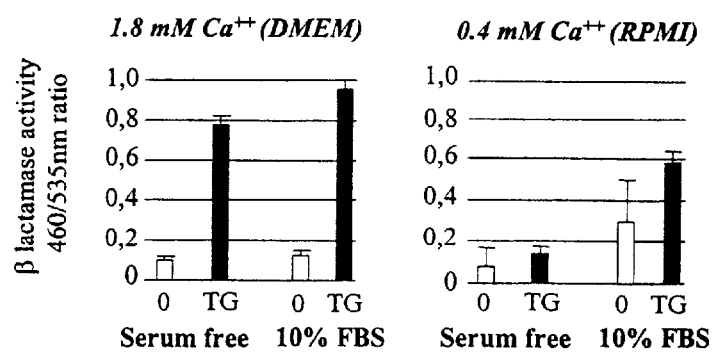
Figure 2C:
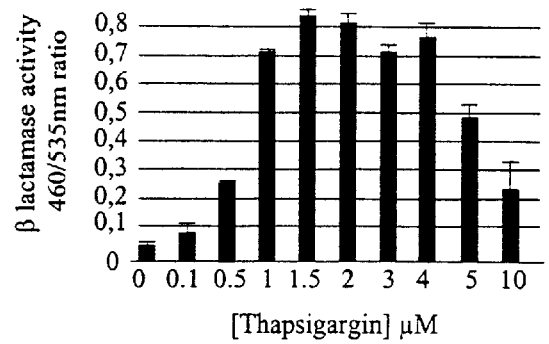

A gene reporter assay (see FIG. 2A for schematic principle) was set up to study the T-cell activation and NFAT-driven gene production related to activation and gating of Icrac. In this test, co-stimulation with PKC activators was avoided, since the assay was made to identify Icrac blockers or inactivators but not PKC inhibitors. However, while thapsigargin alone can trigger a NFAT-related gene production, the resulting β-lactamase activity turned out to be weak in conventional conditions (conventional conditions being 0.4 mM [$Ca^{++}$]. (FIG. 2B). To overcome this problem and design a selective screening assay, we have found that when [$Ca^{++}$]$_0$ was increased to 1.8 mM (instead of about 0.4 mM), the signal to noise ratio became 5-fold higher and suitable for an HTS assay. In addition, it was shown that the gene reporter (β-lactamase) expression was related to the TG concentration from 0 to 1 μM; higher concentrations did not further increase the β-lactamase synthesis (FIG. 2C), and even a decrease was observed at concentrations of 5–10 μM TG.

3. Inhibitors and Activators of NFAT System (Screening Validation)

Several known Icrac activators such as phytohemeagglutinin (PHA), thapsigargin (TG), cyclopiazonic acid (CPA) and antibody against CD28, were tested, and their (Table 1) show that TG is the most active Icrac activator, and, as previously described (22) the combination TG/PMA significantly increases the signal. Okadaic acid (OKA), a PP1A and PP2 phosphatase inhibitor blocked the β-lactamase synthesis, consistent with previous results (23) both on Jurkat cells (FIG. 4) and mastocytes (not shown). Calyculin, another phosphatase inhibitor, blocked the NFAT activation in a dose dependent manner (FIG. 4 and (11)). Cyclosporin (CsA), a calcineurin phosphatase inhibitor, suppressed the β-lactamase synthesis with an $IC_{50}$ at 17 nM (FIG. 5), in good agreement with previous report (18 nM, see (22)). Jurkat cells are thought to lack voltage-dependent $Ca^{++}$ channels. In good agreement with this assumption, specific inhibitors of these channels (Verapamil, Diltiazem and Nifedipine) did not have any effect on the β-lactamase synthesis (FIG. 4) when used at 10 μM. Toxic effects were detected at 50 μM (weak loading, data not shown). Tazobactam, a β-lactamase inhibitor (Ki=0.7 μM) was shown to block both the NFAT-driven (FIG. 4) and the constitutive β-lactamase (CMV-driven) with an $IC_{50}$ at 2 μM.

4. Effect of DMSO

DMSO is a very common vehicle for water-insoluble compounds as well as a well-known anti-inflammatory compound. We tested the effect of this chemical on the different cell lines and different promoters described in this application. As shown in FIG. 6, DMSO has no effect on Jk-CMV-βlac cell β-lactamase (constitutive) synthesis. However, it did inhibit the Jk-NFAT-βlac, p815-NFAT-βlac and HEK-CRE-βlac cells β-lactamase production, with an IC 50 at 1%. Furthermore, Table II indicated that the loading was not modified after DMSO treatment. To further study the DMSO inhibition mechanism, DMSO. CsA and CHX were added at different time after TG addition. The time course of the DMSO and CsA inhibitory effects are very much alike, and both compounds did not block β-lactamase synthesis if added 3 hrs after TG activation, whereas the CHX time course pattern strongly diverged, exhibiting an inhibitory effect when added as long as 4 hrs after TG stimulation, suggesting that the compound acted at the protein synthesis level. This DMSO inhibitory effect is equally detected with HEK-CRE-βlac suggesting that DMSO acted after the $[Ca^{++}]_i$ increase and before the protein synthesis. Confirming these results, $[Ca^{++}]_i$ determination using Fura-2 as probe, showed that this compound had no effect on the Icrac channel itself.

5. High Thoughput Assay

A test on a 3000 compounds sub-library was performed in the following conditions:

Plate preparation and cell stimulation

Seed cells at $10^5$ cells/180 μl/well in DMEM medium (GIBCO Cat #) 90%, FBS 10% into 96-well clear bottom black plates (COSTAR cat #3603). Add 18 μl of thapsigargin (11.1 μM)+2 μL of compound 1 mM in 50% DMSO (i.e. 0.5% final DMSO). Incubate at 37° C., 5% $CO_2$ 90% humidity for 4 h.

Dye loading

12 μl of CCF2-AM 1 mM were vigorously mixed with 60 μl pluronic acid, and then with a 1 ml PEG 400 solution. 40 μl of the resulting solution was added to the wells. Plates were then wrapped into foil, gently agitated at room temperature from 45 min to 2 hrs.

Fluorimeter Assay

Excitation was performed at 405 nm and emission at 460 and 535 nm. The following controls were added in each plate. i) Blank, medium without cells; ii) positive control (100%), JkNFATβ-lac stimulated with thapsigargin; iii) negative control (0%), non-stimulated JkNFATβ-lac.

Ratio calculation was as follow. Mean of blank values was subtracted from the F.U.s (both for the F.U. 460 nm and F.U. 535 nm) and the ratio of resulting values (460/535) estimated. Usually, the negative control values were about 0.010 and the positive control's about 0.400–0.500.

Secondary Screening

To determine whether the selected hits have an effect either upstream or downstream the nuclear factor activation, their potential inhibition of CRE-driven β-lactamase synthesis is checked using HEK cells stably transformed with a CRE3×βlactamase expression vector. The cells are stimulated for 6 hrs with 10 μM forskolin.

Results

The assay showed that the intra and inter-plate standard deviation was not higher than 5% (data not shown). Out of the 3000 test compounds, 17 were screened as Icrac blockers in the assay, and 3 were selected after the secondary assay. This example shows that the method allows efficient, reliable and selective screening of Icrac modulators.

6. Discussion

In this application, a cell-based/gene reporter system is described. It allows convenient analysis of the NFAT activation process, since the amplitude of the inducible signal and the reproducibility of this assay is compatible with the use of 96-wells microtiter plate (preliminary data showed that 384-plate can be as well used with this assay FIG. 7).

Several modulators of the Icrac-related NFAT activation pathway were tested and their effects were found in good agreement with previous reports. Noteworthy, the NFAT-driven gene activation is likely to be a binary event, T-cells remain inactivated until activated (dephosphorylated) NFAT reaches a threshold concentration. The T-cell are then triggered to enter an activated state that is equivalent for all forms and concentration of stimuli (22, 24). In this context, $IC_{50}$S reflected a decrease in the percentage in responder cells rather than in the intensity of the response in individual cells.

An important aspect of the test presented here, is the Icrac-specific stimulus used (i.e. TG) and the fact that PKC pathway was not activated here, leading to a more specific assay. Furthermore, to sort out bona fide Icrac modulators among non-specific compounds, another gene reporter assay involving a different response element (i.e. HEK-CRE-βlac based assay) has been set up, allowing to dramatically reduce the number of false positives. Other secondary low through put assay can be developed such as $^{45}Ca$ uptake and electrophysiology of the Icrac channel. The test is suitable for HTS. Indeed, cells have to receive a mixture of TG and the compound, be incubated at 37° C. for 4 h and loaded with CCF2-AM for 30 min. An other asset of the technique is the β-lactamase substrate. CCF2 is non toxic, ratiometric and stay within cells for several hours. Then, β-lactamase appears to be the most suitable protein for gene reporter assay. Indeed, it can be monitored in living cells (unlike β-galactosidase or luciferase) and, since β-lactamase is a bacterial enzyme, no endogenous activity will cross react in mammalian cells (unlike alkaline phosphatase). But the most attracting feature of the test is that it allows the detection not only of bona fide $Ca^{++}$-inflow blockers, but of molecules acting on Icrac activation level. Since it has been very recently proposed that this activation is the outcome of a scaffolding of several proteins (TRP, IP3 (26, 27) and SNAP25 (18)) any blocker of protein-protein interactions between these components is de facto a modulator of the Icrac activation. This could lead to the discovery of very specific molecules, with predictable low side effects, and not only to non-specific $Ca^{++}$ channel "corks".

During this study, DMSO was checked as a potential non specific β-lactamase blocker. We showed that DMSO blocked NFAT-driven β-lactamase expression both in mastocytes and lymphocytes as well as it blocked the CRE-driven β-lactamase expression in HEK cells with an $IC_{50}$ around 1%. Interestingly, we showed that DMSO inhibitory effect arose between NFAT activation and RNA translation, but did not act as a non-specific protein synthesis blocker. Further studies are needed to accurately spot the intracellular DMSO target. However, we showed that 0.5% DMSO did not hinder the assay and can be used as final concentration. Noteworthy, the pharmacological tools used in this study did not allow to detect differences (if any) between the Icrac channel from T-cells and mastocytes.

Accordingly, the cell based described here substantially facilitates screening procedures and broaden the investigation field aiming at the identification of novel reagents with therapeutic potential in inflammation-, cell proliferation (e.g., cancer)-, auto-immune- or allergy-related pathologies.

1. Robey, E. and Allison J. P. (1995) *Immunol.Today* 16, 306–310.
2. Ghosh, P. et al. (1996). *J.Biol.Chem* 271, 7700–7704.
3. Rao, A., Luo, C., and Hogan, P.G. (1997) *Annu.Rev.Immunol.* 15,707–747.
4. Clipstone, N. A. and Crabtree, G.R. (1992) *Nature* 357, 695–697.
5. Lewis, R. S. and Cahalan, M. D. (1990)*Annu.Rev.Physiol.* 52:415–30,415–430.
6. Berridge, M. J. (1995) *Biochem.J.* 312, 1–11.
7. Fanger, C. M., et al. (1999) *J.Cell Biol.* 131, 655–667.
8. Mason, M. J., et al. (May 11, 1991) *J Biol Chem* 266, 20856–20862.
9. Thastrup et al., PNAS 87 (1990) 2466
10. Am. J. Physiol. 269 (1995) C733
11. Li, W. and Handschumacher (1996) *Biochem.Biophys.Res.Commun.* 219, 96–99.
12. J. Biol.Chem. 270 (1995) 169

13. Zlokarnik, et al. (1998) *Science* 279, 84–88.
14. Flanagan, et al. (Aug. 20, 1991) *Nature* 352, 803–807
15. Loh, C et al. (Mar. 5, 1996) *J.Biol.Chem.* 271, 10884–10891.
16. Hoth, M. and Penner, R. (1992) *Nature* 355, 353–356.
17. Mason, M. J. et al., J. Biol.Chem 266, 20856–20862
18. Yao, et al. (Aug. 20, 1999) *Cell* 98, 475–485.
19. Mattila, et al. (1990) *EMBO J.* 9, 4425–4433.
20. Yamagami, et al. (1998) *Ann N Y Acad Sci* 527 ,87–102.
21. Grynkiewicz, et al. (1985) J.Biol.Chem. 260, 3440–3450.
22. Negulescu, et al. (1994) *Proc.Natl.Acad.Sci.U.S.A.* 91, 2873–2877.
23. Thevenin, C et al.( May 25, 1991) *J.Biol.Chem.* 266, 9363–9366.
24. Karttunen, J. and Shastri, N. (1991) *Proc Natl Acad Sci USA* 88, 3972–3976.
26. Boulay et al. (2000) Proc.Natl.Acad.Sci.USA 96, 14955–14960.
27. Putney, J. W. Jr. (2000) *Proc.Natl.Acad.Sci USA* 96, 14672–14674.

TABLE 1

| Icrac activator | Ratio (460 nm/535 nm) | % total (TG 1 μM) |
|---|---|---|
| TG 1 μM | 0.688 ± 0.035 | 100 |
| PMA 10 nM | 0.012 ± 0.008 | 2 |
| TG 1 μM + PMA 10 nM | 1.648 ± 0.119 | 240 |
| CPA 10 μM | 0.407 ± 0.041 | 59 |
| CPA 10 μM + PMA 10 nM | 1.249 ± 0.032 | 182 |
| PHA 1 μg/ml | 0.280 ± 0.116 | 41 |
| PHA 10 μg/ml | 0.578 ± 0.040 | 84 |
| mAbCD28 30 ng/ml ± PMA 10 nM | 0.020 ± 0.010 | 4 |
| mAbCD28 100 ng/ml ± PMA 10 nM | 0.089 ± 0.023 | 13 |
| mAbCD28 300 ng/ml ± PMA 10 nM | 0.254 ± 0.054 | 37 |
| mAbCD28 1000 ng/ml ± PMA 10 nM | 0.275 ± 0.032 | 40 |

TABLE 2

| treatment | F.U. at 535 nm | | |
|---|---|---|---|
| | Mean | SD | % control |
| Control | 12403 | 173 | 100 |
| DMSO 0.1% | 11957 | 1131 | 99.2 |
| DMSO 1% | 11584 | 1379 | 96.1 |
| DMSO 2% | 11680 | 947 | 97 |
| DMSO 4% | 12980 | 899 | 107.7 |
| DMSO 5% | 13265 | 890 | 110.1 |

What is claimed is:

1. A method for the screening of Icrac blockers, comprising:
   (a) contacting a test compound and an Icrac activator with a population of Icrac-expressing cells, said cells further containing a reporter construct comprising a reporter gene under the control of a NFAT-inducible promoter, said reporter gene encoding a product that hydrolyses a substrate, said cells being incubated in a medium having a calcium concentration of at least 1 mM,
   (b) contacting the cells of a) with a substrate of the reporter gene expression product, and
   (c) determining the activity of the test compound on the calcium release-activated channel by assessing the hydrolysis of the substrate in said cells.

2. The method of claim 1, wherein the reporter gene is the β-lactamase gene.

3. The method of claim 1, wherein the cells are incubated in a medium lacking phorbol ester.

4. A method for the screening of Icrac stimulators, comprising:
   a) contacting a test compound with a population of Icrac-expressing cells, said cells further containing a reporter construct comprising a reporter gene under the control of a NFAT-inducible promoter, said reporter gene encoding a product that hydrolyses a substrate, said cells being incubated in a medium having a calcium concentration of at least 1 mM,
   b) contacting the cells of a) with a substrate of the reporter gene expression product, and
   c) determining the activity of the test compound on the calcium release-activated channel by assessing the hydrolysis of the substrate in said cells.

5. The method of claim 4, wherein the reporter gene is β-lactamase gene.

6. The method of claim 4, wherein the cells are incubated in a medium lacking phorbol ester.

7. A method for the screening of compounds that inhibit calcium release-activated channel (Icrac) activity comprising:
   (a) contacting at least a test compound and a selective, direct or indirect, Icrac activator with a population of Icrac expressing cells, said cells further containing a reporter construct comprising a reporter gene, selected from a β-lactamase gene, under the control of a NFAT-inducible promoter,
   (b) contacting the cells of a) with a substrate of the reporter gene,

SEQUENCE LISTING

<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: NFAT
      binding domain

<400> SEQUENCE: 1
ggaggaaaaa ctgtttcata cagaaggcgt                                    30

(c) determining the activity of the test compounds on the calcium release-activated channel by assessing the hydrolysis of the substrate in said cells, (d) selecting compounds which inhibit at least 40% of the activity (e) screening of the compounds obtained in d) in order to eliminate those which modulate β-lactamase activity in a non-NFAT dependent manner by contacting the compounds selected in d) with a population of cells comprising a reporter construct comprising a β-lactamase gene under the control of a non-NFAT inducible promoter, and selecting compounds which modulate β-lactamase activity in a NFAT dependent manner.

8. The method of claim 7, wherein the reporter construct comprising
a β-lactamase gene is under the control of a CRE-inducible promoter.

9. The method of claims 8, wherein the CRE-inducible promoter comprises between 1 and 8 CRE sequences.

10. A method according to claim 7, wherein said cells are blood cells which contain a reporter construct comprising a reporter gene under the control of a NFAT-inducible promoter.

11. A method according to claim 7, wherein said cells are lymphocytes which contain a reporter construct comprising a reporter gene under the control of a NFAT-inducible promoter.

12. The method of claim 7, wherein the non-NFAT inducible promoter is selected from CRE-inducible promoter, VIP responsive promoter, promoters containing NFκB or JNK reponsive element.

13. A method for the screening of a compound that activates calcium release-activated channel (Icrac) activity comprising:

(a) contacting at least one test compound with a population of Icrac expressing cells, said cells further containing a reporter construct comprising a reporter gene, selected from a β-lactamase gene, under the control of a NFAT-inducible promoter, (b) contacting the cells of a) with a substrate of the reporter gene, (c) determining the activity of the test compounds on the calcium release-activated channel by assessing the hydrolysis of the substrate in said cells, (d) selecting compounds which increase at least 20% of the activity (e) screening of the compounds obtained in d) in order to eliminate those which modulate β-lactamase activity in a non-NFAT dependent manner by contacting the compounds selected in d) with a population of cells comprising a reporter construct comprising a β-lactamase gene under the control of a non-NFAT-inducible promoter, and selecting compounds which modulate β-lactamase activity in a NFAT dependent manner.

14. A method for the screening of Icrac blockers, comprising:

(a) contacting a test compound and an Icrac activator with a population of Icrac-expressing cells, said cells further containing a reporter construct comprising a β-lactamase gene under the control of a NFAT-inducible promoter, said cells being incubated in a medium having a calcium concentration of at least 1 mM, (b) contacting the cells of a) with a substrate of the β-lactamase gene expression product, and (c) determining the activity of the test compound on the calcium release-activated channel by assessing the hydrolysis of the substrate in said cells.

15. The method of claim 14, wherein the cells are incubated in a medium lacking phorbol ester.

16. A method for the screening of Icrac stimulators, comprising:

a) contacting a test compound with a population of Icrac-expressing cells, said cells further containing a reporter construct comprising a β-lactamase gene under the control of a NFAT-inducible promoter, said cells being incubated in a medium having a calcium concentration of at least 1 mM, b) contacting the cells of a) with a substrate of the β-lactamase gene expression product, and c) determining the activity of the test compound on the calcium release-activated channel by assessing the hydrolysis of the substrate in said cells.

17. The method of claim 16, wherein the cells are incubated in a medium lacking phorbol ester.

* * * * *